United States Patent [19]
Hassler

[11] 3,977,247
[45] Aug. 31, 1976

[54] ARRANGEMENT FOR THE MEASUREMENT OF THE FLOW VOLUME OF FLOWING MEDIA

[75] Inventor: Dieter Hassler, Erlangen, Germany

[73] Assignee: Siemens Aktiengesellschaft, Erlangen, Germany

[22] Filed: Dec. 17, 1975

[21] Appl. No.: 641,572

[30] Foreign Application Priority Data
Dec. 23, 1974 Germany............................ 2461264

[52] U.S. Cl............................ 73/194 A; 128/2.05 F
[51] Int. Cl.².......................................... G01F 1/66
[58] Field of Search.............. 73/194 A; 128/2.05 F, 128/2.05 Z

[56] References Cited
UNITED STATES PATENTS
3,554,030   1/1971   Peronneau........................ 73/194 A
3,675,192   7/1972   Fahrbach....................... 73/194 A X FOREIGN PATENTS OR APPLICATIONS
2,148,700   4/1973   Germany........................ 128/2.05 Z Primary Examiner—Charles A. Ruehl
Attorney, Agent, or Firm—Haseltine, Lake & Waters

[57] ABSTRACT

An arrangement for the measurement of the flow volume of flowing media, in particular of blood in its vessels, pursuant to the Ultrasonic-Doppler method, through the utilization of at least two ultrasound transmitter-receivers for the complete, or respectively, partial sounding of the volumetric section of a medium which is to be examined; a Doppler apparatus for determining the output power of the incident Doppler signals during the total, or respectively, partial sounding; as well as a ratio formulator for the output powers. A first ultrasound transmitter-receiver which only partly sounds through a volumetric section is constructed for the receipt of merely such Doppler signals which emanate from a test volume of predetermined dimensions of the flowing medium, which tests volume lies fully within, preferably at the median region, of that volumetric section which is fully sounded through by a further transmitter-receiver, and that a ratio formulator is constructed for the formation of the ratios of the power outputs of Doppler signals from the total volumetric section and from the test volume.

15 Claims, 2 Drawing Figures

ARRANGEMENT FOR THE MEASUREMENT OF THE FLOW VOLUME OF FLOWING MEDIA

FIELD OF THE INVENTION

The present invention relates to an arrangement for the measurement of the flow volume of flowing media, in particular of blood in its vessels, pursuant to the Ultrasonic-Doppler method, through the utilization of at least two ultrasound transmitter-receivers for the complete, or respectively, partial sounding of the volumetric section of a medium which is to be examined; a Doppler apparatus for determining the output power of the incident Doppler signals during the total, or respectively, partial sounding; as well as a ratio formulator for the output powers.

DISCUSSION OF THE PRIOR ART

The flow volume Q of flowing or streaming media is obtained for a suitably formed velocity profile at $Q = F \times \bar{v}$, wherein $F$ is the cross-sectional surface of the flow and $\bar{v}$ a weighted median value of the flow velocity. The median value $\bar{v}$ may be determined pursuant to the Ultrasonic-Doppler method with an arrangement constructed, for example, as is shown in U.S. Pat. No. 3,675,192. For determination of the cross-sectional surface F pursuant to the Doppler method, there has heretofore been available an arrangement pursuant to German Published Pat. No. 1,812,017.

The arrangement pursuant to the German Published Pat. No. 1,812,017 serves primarily for obtaining the internal measurement (radius) of vessels, in particular, blood vessels. The arrangement encompasses two ultrasound transmitter-receivers which are located at a predetermined distance, adjacent each other, and which concurrently project ultrasound onto the vessel which is being examined, for example, the blood vessel, whereby the transmitting-receiving lobe or beam of each transmitter-receiver extensively widens in a direction towards the vessel. Hereby the distance between the two transmitter-receivers is selected so that their transmitting-receiving lobes overlap to some extent in the region of the aimed-at vessel, whereby the transmitting-receiving lobe of the one transmitter-receiver has one side edge thereof just tangent with the assumedly circular vessel and otherwise completely passes through the vessel, whereas the transmitting-receiving lobe of the other transmitter-receiver cuts the vessel with the corresponding lobe edge, thus only partially through-sounding the vessel. Due to this differently intensive sounding, there are produced at the outputs of a Doppler apparatus which is connected to the outputs of the two transmitter-receivers, correspondingly different Doppler signal power outputs. From the ratio between the differently strong or intense Doppler signal power outputs, which is obtained, for example, by means of a divider element connected to the output of the Doppler apparatus, there can then be calculated with the aid of a calculator in conjunction with further calculating magnitudes, such as the distance or spacing between the two transmitter-receivers, as well as the aperture angle between their transmitting-receiving lobes, the radius of the vessel at the sounded location pursuant to a calculation formula, for example, as set forth in claim 9 of German Published Pat. No. 1,812,017. From the radius there can then be obtained the circular cross-sectional surface F of the vessel.

However, on the one hand, the arrangement according to German Published Pat. No. 1,812,017 has the disadvantage that it is technically extremely complex since, for the effectuation of the relatively complicated calculating operations, there are required correspondingly complicated and expensive calculating components. On the other hand, especially with regard to flow volume measurements, it is also quite uncertain in the calculating results since, for effecting the verification of the geometric conditions, such as for example, the circular vessel cross-section, tangential contact of the vessel wall by the column or lobe border of the sounding lobe of a transmitter-receiver and so forth, in actual practice it is often not possible, respectively, difficult to maintain and, on the other hand, at an extensively widening sounding field, it is not possible to have an aiming procedure and, as a result, the screening out of disruptive effects which, for example, also come from adjacent scanned along vessels. As a result there are produced unavoidable measuring errors at the determination of the cross-section already prior to the obtention of the actual flow volume, which falsify the flow volume measurement value at already this location.

SUMMARY OF THE INVENTION

Accordingly, it is an object of the present invention to construct an arrangement of the above-mentioned type which, at a minimum technical demand, affords a much more precise measurement of the flow volume of streaming or flowing media.

The foregoing object is inventively attained in that a first ultrasound transmitter-receiver which only partly sounds through a volumetric section is constructed for the receipt of merely such Doppler signals which emanate from a test volume of predetermined dimensions of the flowing medium, which tests volume lies fully within, preferably at the median region, of that volumetric section which is fully sounded through by a further transmitter-receiver, and that a ratio formulator is constructed for the formation of the ratios of the power outputs of Doppler signals from the total volumetric section and from the test volume.

The present invention is predicated upon the recognition that, at homogeneously through-sounded flow volumes, the power output of the Doppler-displaced signals currently are proportional to the lumen magnitude. At known test volumes $V_p$ and measurable Doppler power outputs $P_p$ from the test volume $V_p$, as well as $P_m$ from the total volumetric section $V_m$, there is then obtained for the last-mentioned the relationship $$V_m = V_p \cdot P_m/P_p \cdot \text{Because } V_m = F_m \cdot b,$$

with $F_m$ as the unknown surface and $b$ as predetermined through the measurements of the transmitting-receiving lobe of the second transmitter-receiver, in effect, the known width of the total volumetric section $V_m$, there is thus obtained for the flow volume $Q$ in the total volumetric section $$Q = \bar{v} \, F_m = \bar{v} \, V_p/b \cdot P_m/P_p.$$

The invention thereby facilitates the obtention of the flow volume without any precedent cross-sectional determination. Measuring errors, which would be caused on the basis of inexact cross-sectional measurement, are thus initially precluded. At the lowest technical demand there is thus produced a measure for the flow volume, which as desired, is extensively freed from any uncertainties in measurement.

The flow volume may be manually calculated from the measured power output values $P_m$, or respectively $P_p$, as well as the known test volumes $V_p$ and the remaining values $\bar{v}$ and $b$ by means of slide rulers or the like. Suitably, however, there should be provided an electronic calculating circuit, whose calculating elements continually electrically determine the flow volume pursuant to the above relationship.

In an advantageous construction of the invention, for limiting the test volume, the first transmitter-receiver should evidence a sharply collimated transmitting-receiving lobe or beam which, with respect to the preferably similarly sharply collimated transmitting-receiving lobe of the second transmitter-receiver, evidences an essentially smaller cross-section and determines with this cross-section the transverse dimension of the test volume, and for assumption of the longitudinal dimension of the test volume, an electronic signal gate should be associated with the first transmitter-receiver, which is adjustable through the intermediary of control elements to the receipt of Doppler signals from merely a predetermined depth region of the volumetric section of the medium. Furthermore, in another advantageous construction of the invention, the first transmitter-receiver should be so arranged within the confines of the transmitting-receiving lobe or beam of the second transmitter-receiver, whereby the main transmitting-receiving directions of both transmitter-receivers essentially coincide. In contrast to the arrangement according to the German Published Pat. No. 1,812,017, wherein the main transmitting-receiving directions of the transmitter-receivers provided therein extend at a spacing in parallel to each other, there is hereby produced an essentially narrower and consequently sharper confined ultrasound-input area with a correspondingly lower disruptive influence over the Doppler signals. Since the ultrasounds of both transmitters-receivers in the essentially more dense back-and-forth path must pass to and from the medium, there are also obtained equal attenuation relationships and thereby proportionality in the power output indication with the same proportionality factor. Additional measuring errors, which can be produced due to different proportionalities, are thereby also initially excluded.

The coincidence may be reached most advantageously in that the first transmitter-receiver is utilized as a relatively small-surfaced ultrasound vibrator which is located in a surface aperture, preferably in the middle, of a further ultrasound vibrator or oscillator with a substantially larger surface whereby, suitably, the small-surfaced vibrator, as well as its encompassing large-surfaced vibrator, are operatively interconnectable and, in the interconnected condition, form the second transmitter-receiver through the entire surface.

BRIEF DESCRIPTION OF THE DRAWINGS

Further advantages and details of the invention may now be ascertained from the following description of an exemplary embodiment thereof, taken in conjunction with the accompanying drawings; in which.

DETAILED DESCRIPTION

Figure 1:
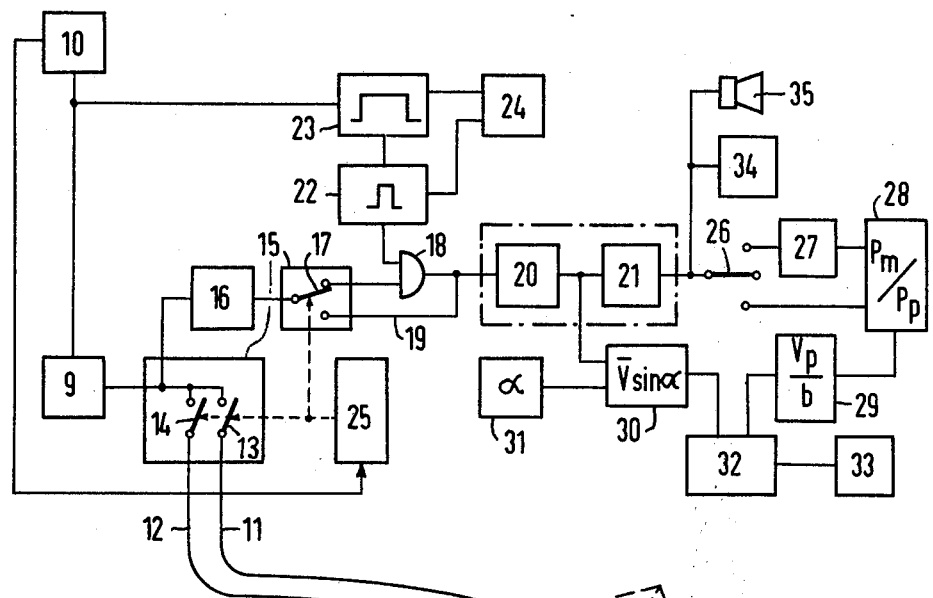
FIG. 1 schematically illustrates an arrangement for the measurement of the flow volume of flowing media which is constructed pursuant to the present invention.

Referring now to FIG. 1 of the drawings, an Ultrasonic-Doppler applicator is designated by reference numeral 1, which encompasses a carrier part 2 and which is formed, for example, of a plastic material on whose application surface there are arranged two ultrasound vibrators 3, 4 (thin small piezo-electric crystal plates) having different surfaces. The smaller-surfaced vibrator 3 hereby is so introduced into a surface aperture formed in the middle of the large-surfaced vibrator 4, that the reflective surfaces of both vibrators are presently located within a common plane. The surface configuration of both vibrators is square, wherein the side dimensions of the squares are so selected that the smaller vibrator 3 possesses a surface $F_1$ in the range of 4 to 20 mm², and larger vibrator 4 encompassing the smaller vibrator 3, together with the first, in contrast therewith has a surface $F_2$ in the range of 50 to 200 mm².

The applicator 1 is so positioned on the skin 5 of a person being probed whereby, in the operative condition of the small-surfaced vibrator 3, the smaller transmitting-receiving lobe or beam 6 traverses the blood stream of a blood vessel 7 which extends invisibly in the tissue below the skin only within a very small part section which contains the test volume $V_p$. The transmitting-receiving lobe 8 of the operatively interconnected vibrators 3 and 4, in contrast, detects the entire vessel 7 within a total volumetric section $V_m$ having the length $b$. The small dimensioned test volume $V_p$ is located precisely in the middle of the total volumetric section $V_m$. While the cross-section measurements of the test volume $V_p$ through the cross-section $F_1$ of the sharply collimated transmitting-receiving lobe or beam 6 of the small-surfaced vibrator 3 are predetermined, for the length limitation a there serves a signal gate 18 in the electrical control and, respectively, processing component of the applicator, which is adjustable to the receipt of Doppler signals merely from the depth region a of the total volumetric section $V_m$.

The electrical control and, respectively, processing installation of the applicator 1 contains a high-frequency transmitting oscillator 9 which, in synchronism with a pulse generator 10, transmits high-frequency stimulating impulses to the vibrators 3, or respectively 3 and 4, through the conductors 11, respectively 11 and 12. The selective connection of the vibrator 3, or respectively both vibrators 3 and 4, to the transmitting oscillator 9 is effectuated by means of control switches 13, respectively 14, of a switching device 15.

Designated by reference numeral 16 is a receiver-amplifier for the echo-signals received from the oscillators 3, or respectively 3 and 4, from the medium flowing in the vessel 7. The output of the receiver-amplifier 16 is indirectly connected, by means of a further switch 17 of the switch device 15, through an electronic gate 18 with a Doppler apparatus 20, 21, or directly through a gate-bridging conductor 19. The Doppler apparatus thereby essentially encompasses a demodulator 20 for effecting the the demodulation of the received electrical ultrasound signals, as well as a power output measuring device 21 for the measurement of the power output of the Doppler signals. Associated with the electronic gate 18 are two monostable flip-flops 22 and 23.

The flip-flop 23 hereby produces output impulses in the transmitting beat of the ultrasound-transmitting impulses of the small-surfaced vibrator 3, whose duration determines the depth distancing of the test volume $V_p$ from the vibrator 3. The flip-flop 22, which is respectively actuated by the end of an output impulse of the flip-flop 23, in contrast therewith, produces much shorter output impulses, whose duration determines the depth region which is to be scanned, meaning, determines the length a of the test volume $V_p$. During the duration of the last-mentioned impulses, the electronic signal gate 18 is presently opened for incident Doppler signals. For varying the depth distancing, as well as also for varying the length a of the depth region which is to be scanned, the monostable flip-flops 22, 23 additionally have an adjusting element 24 associated therewith, by means of which the output impulses of the flip-flops may be adjusted or set to different lengths. Finally, the reference numeral 25 relates to an actuating element for the actuation of the individual switches 13, 14, 17 of the switching device 15. Identified by reference numeral 26 is an output switch of the Doppler apparatus 20, 21, which applies to a divider element 28, across a storage element 27, power output signals which are measured during the test volume measurement, while the power output signals which are received during the total volumetric section measurement are transmitted directly to the divider element 28. The divider element 28 presently forms the ratio $P_m/P_p$ of the power outputs of the Doppler signals from the total volumetric section $V_m$ and the test volume $V_p$. For obtaining the current flow volume Q there finally serves a calculating circuit 29 through 32. Hereby, the calculating element 29 is a multiplier element (proportionality element), which multiplies the power output ratio signal of the divider element 28 with the quotient $V_p/b$ from the known test volume $V_p$ and the length b of the total volumetric section $V_m$. The element 30 encompasses a device for obtaining a weighted median value, ($\bar{v}$ sine $\alpha$) of the flow velocity of the median in the total volumetric section $V_m$, whereby $\alpha$ represents the ultrasound-incidence angle into the median. For instance, the installation 30 may correspond to that disclosed in U.S. Pat. No. 3,675,192. When the median value $\bar{v}$ of the velocity $v$, as well as the incidence angle $\alpha$ are measured independently of each other, then, as is indicated in an exemplary manner in FIG. 1, there is correspondingly obtained in the installation 30, from the median value signal of the velocity and the angle (element 31), the signal $\bar{v}$ sine $\alpha$. The output signals of that of the element 29 and of the installation 30 are finally multiplied with each other in a multiplier element 32. Obtained hereby is the measure for the flow volume Q and the total volumetric section $V_m$ of the vessel 7 pursuant to the relationship $$Q = (\bar{v} \text{ sine } \alpha) \cdot V_p/b \cdot P_m/P_p.$$

The presently obtained flow volume value Q is indicated, or respectively registered on an indicator or registration apparatus 33.

For searching out the current vessel 7, respectively, for the correct insertion of the test volume $V_p$ into the vessel, there serves a Doppler signal indicator apparatus 34, which preferably also has associated therewith a sound generator 35 (loudspeaker).

The manner of functioning of the arrangement pursuant to FIG. 1 is obtained as follows:

Before commencing the actual flow volume measurement, there must first be located the blood vessel 7 which is provided for the measurement, and the test volume $V_p$ adjusted in the correct position within the vessel. Hereby, through actuation of the switch 13, the small-surfaced vibrator 3 is placed into operation. By means of the switch 17 which is connected to the conductor 19, meaning at a short-circuited electronic signal gate 18, the applicator 1 is displaced for so long along the skin 5 over the blood vessel 7, until the Doppler signals which are indicated by means of the indicator apparatus 34 evidence the highest intensity, respectively, the Doppler signals which are rendered audible through intermediary of the loudspeaker 35, evince the maximum sound or loudness intensity. The transmitting-receiving beam 6 of the small-surfaced vibrator 3 at that instance passes through the vessel 17 precisely in the cross-sectional middle thereof.

Thereafter, through switching back of the switch 17 into the illustrated position, the electronic signal gate 18 is connected between the receiver-amplifier 16 and the Doppler apparatus 20, 21. At a previously set impulse width of the output signals of the monostable flip-flop 22, the impulse width of the output signals of the flip-flop 23 is now adjusted for so long through the adjusting element 24, until there is indicated at the indicator element 34, respectively loudspeaker 35, a new maximum intensity of the Doppler signals. The test volume $V_p$ is thereby restricted to a region immediately about the middle axis of the vessel 7.

After the vessel positioning and setting of the test volume $V_p$ has been carried out, the switch 26 at the output of the Doppler apparatus 20, 21 is applied from the zero position to the input of the storage element 27, the latter of which stores the power output of the Doppler signals from the test volume $V_p$ measured by the Doppler apparatus. Subsequently carried out is the power output measurement in the total volumetric section $V_m$. For this purpose there is closed the switch 14, the reversing switch 17 again connected to the bridging or bypass conductor 19 and furthermore, by means of the switch 26, the output of the Doppler apparatus is directly connected with the divider element 28. Since both vibrators 3 and 4 are now commonly placed in operation, Doppler signals are received from the total volumetric section $V_m$ of the vessel 7, whose power output is again obtained from the Doppler apparatus 20, 21 and, together with the stored power output signal from the test volume measurement, transmitted to the divider element 28. The divider element 28 now forms the quotient from the power output $P_m$ of the Doppler signals from the total volumetric section $V_m$, as well as the power output $P_p$ of the Doppler signals from merely the test volume $V_p$. Through instantaneous electronic calculation of the ratio signal $P_m/P_p$ by means of the calculating magnitudes which are present in the calculating elements 29, 30 and, as required, in 31, there is then directly obtained at the indicator apparatus 33, directly the flow volume of the blood in the total volumetric section $V_m$ of the vessel 7.

Figure 2:
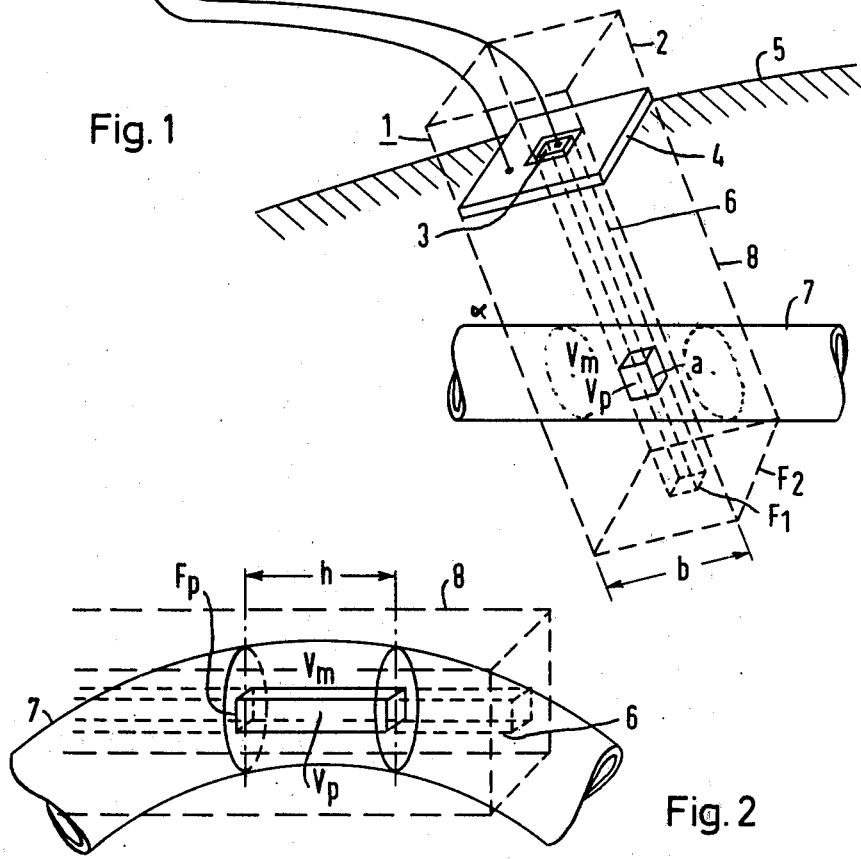
FIG. 2 illustrates fragmentary portion of the arrangement of FIG. 1 as applied to a curved vessel which is being measured.

The arrangement pursuant to FIG. 1 is suitable for use in the flow volume measurement of straight as well as twistedly extending vessels. In the measurement of twistedly extending vessels, for example, in the aorta bends extending out from the sternum, which allows for merely one ultrasound beaming direction along the longitudinal direction of the bend, it is recommended, as is indicated in FIG. 2 in an exemplary manner, that there be carried out the test volume measurement, as well as the total volumetric measurement carried at a switched-in gate 18. Hereby, the open gate time period should suitably be equal for both measurements and merely, in contrast with the measurement of straight vessels, be somewhat lengthier for attaining wider volumetric sections. Since the angle of incidence relative to the flow direction of the blood is almost zero, and the test volume $V_p$, as well as the total volumetric section $V_m$ have the same length, for example, evidencing the length h pursuant to FIG. 2, there is obtained the simplified relationship for the flow volume Q in the twisted region $$Q = \overline{v} \cdot P_m/P_p \cdot F_p,$$

wherein $F_p$ represents the cross-sectional surface of the test volume $V_p$.

While there has been shown what is considered to be the preferred embodiment of the invention, it will be obvious that modifications may be made which come within the scope of the disclosure of the specification.

What is claimed is:

1. In an arrangement for the measurement of the flow volume of flowing media, particularly blood in its vessels, pursuant to the Ultrasonic-Doppler method, including at least two ultrasound transmitter-receivers for at least the partial sounding of the volumetric section of a medium; a Doppler apparatus for determining the output power of the incident doppler signals during the at least partial sounding; and a ratio formulator for the output powers of said signals, the improvement comprising: a first one of said ultrasound transmitter-receivers partially sounding a volumetric section and being adapted to receive merely such doppler signals emanating from the flowing medium of a test volume having predetermined dimensions; a second one of said ultrasound transmitter-receivers fully sounding a total volumetric section, said test volume being located completely within said last-mentioned volumetric section; and said ratio formulator including means for forming the ratio of the power outputs of the doppler signals from the total volumetric section and the test volume.

2. An arrangement as claimed in claim 1, said first transmitter-receiver providing a sharply collimated transmitting-receiving beam for limiting the test volume, said beam having a substantially smaller cross-section relative to a sharply collimated transmitting-receiving beam of said second transmitter-receiver so as to define the transverse dimensions of said test volume with said cross-section; an electronic signal gate being associated with said first transmitter-receiver for predetermining the longitudinal dimension of said test volume; and control means connected with said signal gate for adjusting the latter to the receipt of doppler signals from merely a predetermined depth region of the total volumetric section of the medium.

3. An arrangement as claimed in claim 2, said first transmitter-receiver being positioned within the confines of the transmitting-receiving beam of said second transmitter-receiver and oriented so that the main transmitting-receiving directions of both said transmitter-receivers essentially coincide.

4. An arrangement as claimed in claim 3, said first transmitter-receiver comprising a relatively small-surfaced ultrasound vibrator; and said second transmitter-receiver comprising a ultrasound vibrator having a surface substantially larger than that of the first ultrasound vibrator, said small-surfaced vibrator being located in an aperture formed in the surface of the larger vibrator.

5. An arrangement as claimed in claim 4, said small-surfaced vibrator being positioned in the center of said larger vibrator.

6. An arrangement as claimed in claim 4, comprising means for operatively interconnecting said small-surfaced vibrator and the encompassing large vibrator, said vibrators forming the total surface of said second transmitter-receiver in their operatively interconnected condition.

7. An arrangement as claimed in claim 4, said first and second vibrators having surface ratios in the magnitude of about 1:10, said small-surfaced vibrator having a surface of about 4 to 20 mm$^2$ and the larger vibrator a surface of about 50 to 250 mm$^2$.

8. An arrangement as claimed in claim 4, said first and second vibrators each having substantially rectangular surface configurations.

9. An arrangement as claimed in claim 4, said first and second vibrators each having substantially square surface configurations.

10. An arrangement as claimed in claim 4, comprising switching means for obtaining the power output of doppler signals merely from said test volume, including a first switch for separately connecting said small-surfaced vibrator to a common high-frequency transmitting oscillator and to a receiver-amplifier, and a second switch for actuation of the electronic signal gate for depth scanning between said receiver-amplifier and said doppler apparatus.

11. An arrangement as claimed in claim 10, comprising a third switch for connecting the large vibrator encompassing the small-surfaced vibrator, in addition to said small-surfaced vibrator, to said transmitting oscillator and receiver-amplifier for obtaining the power output of doppler signals from the total volumetric section, said second switch being switchable to short-circuiting bypass of said electronic signal gate through direct connection between said receiver-amplifier and said doppler apparatus.

12. An arrangement as claimed in claim 4, comprising two monostable flip-flops for control of said electronic signal gate during test volume measurement, one said flip-flop generating output impulses in the transmitting pulse of the ultrasound transmitting impulses of the small-surfaced vibrator, said output impulses having a duration determinative of the depth distance of the test volume from the vibrator, the other flip-flop being contacted by the end of each said output impulse and producing a comparatively much shorter output impulse having a duration determinative of scanned depth region and the length of said test volume and forming the opening impulse for said electronic signal gate.

13. An arrangement as claimed in claim 12, comprising an adjusting element being connected to said monostable flip-flops for setting different output impulse lengths so as to vary the depth distance and the length of the scanned depth region.

14. An arrangement as claimed in claim 1, comprising means for obtaining a weighted median value ($\overline{v}$ sine $\alpha$) of the flow velocity of the medium in said total volumetric section ($V_m$), wherein $\alpha$ represents the ultrasound incidence angle into the medium; multiplier elements being connected to said means and to the doppler signal power output ratio formulator for calculating from the velocity median value signal ($\overline{v}$ sine $\alpha$), the power output ratio signal ($P_m/P_p$), from the test volume ($V_p$), and from the width of the transmitting-receiving beam of the second transmitter-receiver obtained length ($b$) of the total volumetric section, the flow velocity $Q$ pursuant to the relationship $$Q = (\overline{v} \text{ sine } \alpha) \cdot V_p/b \cdot P_m/P_p.$$

15. An arrangement as claimed in claim 2, said second transmitter-receiver being adjustable through said electronic signal gate during total volume measurement to the receipt of doppler signals from a predetermined depth region.

* * * * *